United States Patent [19]

Tye et al.

[11] Patent Number: 5,357,021
[45] Date of Patent: Oct. 18, 1994

[54] REACTIVE CARBODIIMIDE COMPOSITIONS

[75] Inventors: Anthony J. Tye, Toledo; George G. Beck, Whitehouse; Patrick J. Mormile, Bowling Green, all of Ohio

[73] Assignee: BASF Corporation, Parsippany, N.J.

[21] Appl. No.: 95,076

[22] Filed: Jul. 21, 1993

[51] Int. Cl.$^5$ ............................................. C08G 18/30
[52] U.S. Cl. ....................................... 528/28; 528/44; 528/59; 528/67; 528/69; 528/71; 528/74; 564/252
[58] Field of Search ....................... 528/28, 44, 59, 67, 528/69, 71, 74; 564/252

[56] References Cited

U.S. PATENT DOCUMENTS 5,264,518 11/1993 Amano ................................. 528/44

*Primary Examiner*—Maurice J. Welsh
*Attorney, Agent, or Firm*—Michael R. Chipaloski

[57] ABSTRACT

Novel reactive carbodiimide compounds and their method of preparation are disclosed. These reactive carbodiimide compounds are especially useful in automotive paint compositions and more particularly in low volatile organic content (VOC) automotive paint compositions.

7 Claims, No Drawings

REACTIVE CARBODIMIDE COMPOSITIONS

FIELD OF THE INVENTION

The present invention relates to novel reactive carbodiimide compounds and to their method of preparation. The novel reactive carbodiimide compounds are especially useful in automotive paint compositions.

Automotive paint compositions comprise pigmented base coat formulations, single stage topcoat formulations, clear coat formulations, base coat—clear coat compositions, primer surfacer and sealer compositions.

BACKGROUND OF THE INVENTION

The present invention is directed to novel carbodiimide compounds and to their method of preparation. Such compounds find use in ambient cure automotive paint compositions.

Carbodiimide compounds are known to react with a carboxyl group at ambient temperatures to form an N-acyl urea. The reaction can be represented by

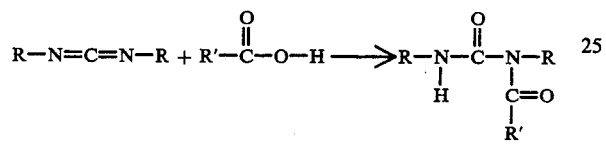

For this reason, this chemistry has been employed to cross-link link or cure carboxyl containing coating compositions at ambient temperatures. Commercial poly-carbodiimide cross-linkers are available and typically are based on aliphatic and cycloaliphatic isocyanates.

According to one aspect of the present invention, an improved coating composition containing the novel carbodiimide compounds with improved drying, improved pot life, ambient curing and durability without the known harmful effects of an isocyanate cure are disclosed.

Any substrate material can be coated with the coating composition according to the present invention. These substrate materials include such things as glass, metal, ceramics, paper, wood and plastic. Coating systems formed using the present invention are particularly adapted for metal substrates and specifically as an automotive refinish system. The substrates may be uncoated material or can be primed. The substrate may also be coated with paint products applied at the time of manufacture. The coating composition can be applied using conventional spray equipment or high volume/low pressure spray equipment.

One of the major difficulties found in this technology and especially in solvent based coating systems is that the reaction tends to take place too rapidly, rendering a two-component coating system with an unusably short pot-life. Some strategies have been developed to retard the carbodiimide/carboxyl reaction to improve pot-life such as salting with tertiary amines, using low acid value coreactants or introducing latent reactive groups. These strategies, however, will either compromise the ultimate film properties, not succeed in sufficient pot-life extension, or both. A slower reacting, light colored, carbodiimide species is therefore desired to overcome the problems of the prior art without special processing or by-products that require disposal during manufacture.

SUMMARY OF THE INVENTION

The Invention defined herein is directed to specific carbodiimide compounds and to their method of preparation. The present invention also describes curable coating compositions containing said carbodiimide.

The carbodiimide compounds can be defined by the following structural formula:

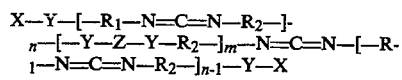

Wherein:
m is from 0 to 1
n is from 1 to 10
$R_1$ = A divalent hydrocarbon residue from a diisocyanate having a tertiary hydrocarbon such as:

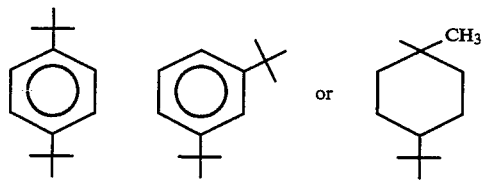

$R_2$ = A divalent hydrocarbon residue from a diisocyanate selected from:

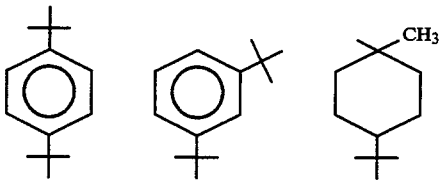

or residues from aliphatic, branched aliphatic or cycloaliphatic diisocyanates, including biurets, allophonates, isocyanurates or uretdiones thereof.
X = Any radical with substituents that are unreactive towards a carbodiimide. For example:
Aliphatic, branched aliphatic, cycloaliphatic or aromatic hydrocarbon, organosilane or salted sulfonic acid radicals.
Or:
A polymeric radical, for example, a polyether polyester, polyurethane, acrylic resin, polycarbonates and mixtures thereof.

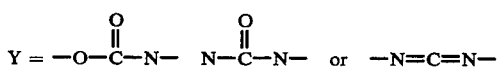

Z = A polyvalent radical with substituents that are unreactive towards a carbodiimide to function as an extending or branching site.
For example:
Aliphatic, branched aliphatic, cycloaliphatic or aromatic hydrocarbon, organosilane or salted sulfonic acid radicals. Or:
A polymeric radical, for example, a polyether, polyester, polyurethane, acrylic resin, polycarbonates and mixtures thereof.

The process for the preparation of carbodiimides and poly-carbodiimides are well known in the art. The classical approach to synthesizing carbodiimides compounds has been to desulfurize N,N'-disubstituted thioureas using mercuric oxide to abstract hydrogen sulfide. This method generally provides good yields, however, has the disadvantage of requiring mercury compounds and yielding sulfur by-products.

N,N'-disubstituted ureas may be dehydrated using tosyl chloride in the presence of triethylamine or by using the procedures taught in U.S. Pat. No. 5,117,069. These methods also yield by-products that require disposal.

In addition to the preparation of carbodiimides by the elimination of ligands from the N—C—N skeleton, another useful scheme involves the addition of N to C—N such as the reaction of isocyanate with phosphoramidate or the preferred method of the catalyzed cycloreversion procedure between two isocyanate groups, accompanied by the loss of $CO_2$. This can be represented by:

$$2\ R-N=C=O \xrightarrow{\text{catalyst}} R-N=C=N-R + CO_2$$

This method has the advantage of using readily available isocyanates and yielding a gaseous by-product. Examples of this method of polycarbodiimide systhesis has been taught in U.S. Pat. Nos. 5,081,173 and 5,047,588.

Polycarbodiimides useful to automotive coatings are those prepared from aliphatic and cycloaliphatic isocyanates. Polycarbodiimides prepared from aromatic isocyanates are generally high in color and of low reactivity at ambient temperatures. Furthermore, undesirable UV induced effects are common when aromatic groups are conjugated with an isocyanate or the reaction products of isocyanates, due presumably to the creation of quinoid-like structures. Mixed aliphatic-/aromatic polycarbodiimides may also be high in color, depending on the relative amount of the aromatic component, require special processing and are suspect for UV durability for reasons just mentioned.

Examplary aliphatic and cycloaliphatic mono and polyisocyanates include: butyl isocyante, cyclohexyl isocyanate, octadecyl isocyanate, 1,4-tetramethylenediisocyanate, 1-6-hexanediisocyanate, 1,12-dodecanediisocyanate, 2,2,4- and 2,4,4-trimethylhexamethylenediisocyanate, 1,4-cyclohexanediisocyanate, bis(4-isocyanatocyclohexyl)methane, isophorone diisocyanate, dipentenediisocyanate, trimers (isocyanurates and biurets) of 1,6-hexamethylenediisocyanate or isophoronediisocyanate and uretdione of isophorone diisocyanate or hexamethylene—diisocyanate.

Especially useful polycarbodiimides have been prepared from diisocyanates comprised of hydrocarbon radicals with tertiary carbons such as:

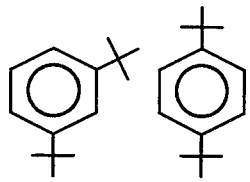

Commercially available diisocyanates fulfilling this criteria are meta and para-tetramethylenediisocyanate(m-and p-TMXDI). Although these isocyanate compounds have aromatic character, the isocyanate groups are removed from the aromatic ring and shielded by saturated carbon atoms. As expected, these isocyanate compounds behave as aliphatic isocyanates in reactivity and properties. The preferred diisocyanate, for reasons of availability and handling is the meta isomer.

U.S. Pat. No. 4,419,294 teaches the preparation of mono or polyfunctional carbodiimides from meta or para TMXDI or dipentenediisocyanate, however the resulting oligomers remain isocyanate functional, with the intended use as isocyanate cross-linkers.

The polycarbodiimide can be prepared entirely from TMXDI or from a mixture of TMXDI and another aliphatic isocyanate compound.

The preferred catalyst. for reasons of efficacy and availability is 3-methyl-1-phenyl-2-phosphonolene-1-oxide. Additional catalysts for the preparation of carbodiimides are described in U.S. Pat. No. 3,426,025.

In the synthetic process, chain termination may be accomplished by the introduction of a stoichiometric amount of a monofunctional isocyanate early in the process or by adding a monofunctional compound with a group that is preferentially reactive with an isocyanate group, for example, hydroxy, primary or secondary amine, at a predetermined conversion. In this manner, other functional groups, unreactive with the carbodiimide groups may be introduced, such as alkoxy silane or water miscible polyethylene oxide groups. A polyfunctional hydroxy or amine compound may be added at an intermediate stage in the synthesis to allow for extension or branching of the polymer.

Conversion of isocyanate can be monitored using the ASTM method D-11638-74 NCO titration. Evolved $CO_2$ may also be measured and used as an indicator of extent of conversion.

The tendency of gel formation at high conversion, common with aliphatic and cycloaliphatic diisocyanates, is reduced with increasing relative percentages of m-TMXDI.

Suitable temperature ranges are from 120 to 170 deg. C. preferably from 140–160 deg. C.

Solvents may be used in processing. Suitable solvents are those that do not have an active hydrogen functionality and have a sufficiently high boiling point to allow the desired reaction temperature. These include aromatic hydrocarbons, ketones and esters.

Based on past experience with aliphatic and cycloaliphatic based carbodiimides, one would expect this carbodiimide to react similarly. However, as observed from solution gel times, this particular carbodiimide will unexpectedly react an order of magnitude slower than those prepared from the conventional aliphatic isocyanates. For this reason, the novel polycarbodiimide of the invention can be used alone, blended with other polycarbodiimides or synthesized as a hybrid polycarbodiimide containing m-TMXD1 and some other aliphatic or cycloaliphatic isocyanate to allow a multi-component system with a carboxyl containing component, available or in-situ generated. Such a carbodiimide compound containing blend has been found to have a controllable pot-life without requiring any of the aforementioned strategies used to retard the carbodiimide/carboxyl reaction.

Novel, TMXDI based polycarbodiimides as discussed herein, may also be used as a cross-linker in water based paint compositions. Water dispersability can be facilitated by attaching a water soluble group or polymer to the polycarbodiimide backbone. Paint compositions utilizing the instant polycarbodiimides are disclosed in more detail and claimed in copending patent applications 08/095,079, 08/095,233 and 08/095,080. The disclosure of each application is incorporated herein by reference.

DETAILED DESCRIPTION OF THE INVENTION

The Invention defined herein is directed to carbodiimide compounds and to their method of preparation. The present invention also describes curable coating compositions containing said carbodiimide.

The carbodiimide compounds can be defined by the following structural formula:

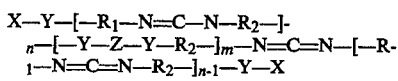

Wherein:
m is from 0 to 1
n is from 1 to 10
$R_1$ = A divalent hydrocarbon residue from a diisocyanate having a tertiary hydrocarbon such as:

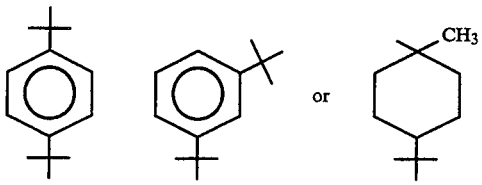

$R_2$ = A divalent hydrocarbon residue from a diisocyanate selected from:

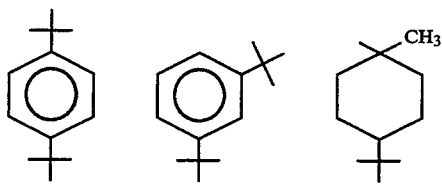

or residues from aliphatic, branched aliphatic or cycloaliphatic diisocyanates, including biurets, allophonates, isocyanurates or uretdiones thereof.
X = Any radical with substituents that are unreactive towards a carbodiimide. For example:
Aliphatic, branched aliphatic, cycloaliphatic or aromatic hydrocarbon, organosilane or salted sulfonic acid radicals.
Or:
A polymeric radical, for example, a polyether polyester, polyurethane, acrylic resin, polycarbonates and mixtures thereof.

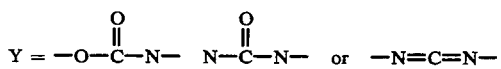

Z = A polyvalent radical with substituents that are unreactive towards a carbodiimide to function as an extending or branching site.
For example:

Aliphatic, branched aliphatic, cycloaliphatic or aromatic hydrocarbon, organosilane or salted sulfonic acid radicals.
Or:
A polymeric radical, for example, a polyether, polyester, polyurethane, acrylic resin, polycarbonates and mixtures thereof.

The polycarbodiimides of the invention can be prepared in a variety of ways. In a synthesis, the methods described in U.S. Pat. No. 5,047,588 can be utilized where the carbodiimides are prepared by the reaction of mono-, di-, and optionally tri- isocyanates, with the easiest structures to conceptualize being based on mono- and diisocyanates in the molar ratio of about 2:1 to about 2:10 mono-diisocyanates to yield the carbodiimide, with the evolution of carbon dioxide, by the following equation:

This process usually requires a catalyst, and a preferred catalyst is, according to the patent, 3-methyl-1-phenyl-2-phospholene-1-oxide.

The physical and chemical attributes of the polycarbodiimide cross-linker are determined empirically. The relative percentage of m-TMXDI, molecular weight, functionality, branching or extending components and capping agents are experimentally balanced to the acidic coreactant to achieve the desired properties of the ultimate coating composition.

In the preferred synthetic procedure, a reaction vessel, equipped with a heating and a cooling element, agitation, condenser and an inert gas subsurface sparge, is charged with m-TMXDI and optionally an aliphatic or cycloaliphatic diisocyanate. If the capping agent is an isocyanate functional compound, a stoichiometric amount is also charged at this stage.

Solvents may be used in the synthesis to reduce the viscosity of the reaction mass. Suitable solvents are those that are non-reactive such as aromatic hydrocarbons, aliphatic esters, glycol ether esters, glycol diesters or ketones, if primary amines are not used in the synthesis. The solvent should have a sufficient boiling point to allow the preferred reaction temperatures.

Catalyst is usually introduced as a solution in a dry, non-reactive solvent, such as xylene. The preferred catalyst is 3-methyl-1-phenyl-2-phospholine-1-oxide at levels between 0.1 and 1.5 molar %.

The reactants are heated to 140–160 C. with an inert gas sparge, typically nitrogen, to facilitate the loss of $CO_2$ and held at that temperature until the % isocyanate value is about 50% of the charge. If the capping agent is not an isocyanate compound, the mixture is then cooled to 60–80 C.

At this stage a stoichiometric amount of capping and perhaps branching or extending components are introduced to the reaction vessel. The amount of the capping agent would depend on the desired polymer chain length. The contents of the reaction vessel is held for several hours at 60–80 C. until the change in isocyanate value becomes constant.

The temperature is then increased to 140–160 C. and the mixture is held at that temperature until the isocyanate is no longer detected. The progress of the reaction may be monitored with an infrared spectrometer, observing the emergence of the carbodiimide peak (at approximately 2125 cm$^{-1}$) and the disappearance of the isocyanate peak (at approximately 2260 cm$^{-1}$).

The viscosity of the finished carbodiimide resin may then be adjusted by the addition of non-reactive solvents.

DESCRIPTION OF THE PREFERRED EMBODIMENTS

The invention detailed herein can additionally be used for the preparation of curable coating compositions by combining with the novel carbodiimide claimed herein a component (oligomer or polymer) bearing structural moeties capable of reacting with the said structural carbodiimide moieties. Such reactive structural moieties can include carboxy, hydroxy, amine, anhydride and the like.

The examples which follow illustrate the invention in various useful embodiments, but are not intended to limit the invention in any way.

EXAMPLE 1

A one liter, 3-neck flask, fitted with a condenser, an agitator, thermocouple and subsurface nitrogen inlet was charged with 195.4 gms. (0.8 moles) meta-tetramethylxylene diisocyanate, 200.0 gms. of xylene, and 15.8 gms. (0.008 moles) of a 9.74 wt. % solution of 3-methyl-1-phenyl-2-phospholene-1-oxide in xylene. A nitrogen sparge was followed by a slow subsurface nitrogen stream that continued throughout the synthesis. Under agitation, the temperature was maintained at 145–150 degrees C. for 10.5 hrs. 15.8 gms. (0.008 moles) of a 9.74 wt. % solution of 3-methyl-1-phenyl-2-phospholene-1-oxide in xylene was then charged to the mixture. The temperature was maintained at 145–150 degrees C. for an additional 12.5 hrs. and another 15.8 gms. (0.008 moles) of the 9.74 wt. % solution of 3-methyl-1-phenyl-2-phospholene-1-oxide in xylene was charged. The temperature was maintained at 145–150 degrees C. for 14 hrs., resulting in a % NCO value (ASTM D2572-87) of 4.23%. The temperature was reduced to 110 degrees C. and 23.7 gms. (0.32 moles) of n-butanol was charged to the mixture. The temperature was maintained at 110 degrees C. for 2.5 hrs., then the temperature was increased to 150 degrees C. and maintained at that temperature for 35 hrs., resulting in a % NCO value of 0.34%. The temperature was reduced to 110 degrees C. and 1.8 gms. (0.02 moles) of n-butanol was charged to consume the remainder of the unreacted isocyanate groups. The temperature was maintained at 110 degrees C. for 2.75 hrs., resulting in an % NCO value of zero.

Infrared analysis confirmed the emergence of carbodiimide functionality (2125 cm$^{-1}$) and the disappearance of isocyanate functionality (2260 cm$^{-1}$) throughout the synthesis.

The non-volatile content was 62.3% measured at 110 degrees C./ 1 hr. and reduced to 51.7% with xylene. The carbodiimide equivalent weight (based on non-volatile.) was 284 by procedure of Zarembo and Watts (*Microchem. J. Symp. Ser.*, 2,591 (1962), (298 theoretical equivalent weight). A weight average molecular weight of 2666 was determined by gel permeation chromatography relative to polystyrene standards.

EXAMPLE 2

A one liter, 3-neck flask, fitted with a condenser, an agitator, thermocouple and subsurface nitrogen inlet was charged with 156.3 gms. (0.64 moles) meta-tetramethylxylene diisocyanate, 35.6 gms. (0.16 moles) of isophorone diisocyanate, 180.0 gms. of xylene, and 15.8 gms. (0.008 moles) of a 9.74 wt. % solution of 3-methyl-1-phenyl-2-phospholene-1-oxide in xylene. A nitrogen sparge was followed by a slow subsurface nitrogen stream that continued throughout the synthesis. Under agitation, the temperature was maintained at 145–150 degrees C. for 9.5 hrs. The temperature was reduced to 110 degrees C. and 23.7 gms. (0.32 moles) of n-butanol was charged to the mixture. The temperature was maintained at 110 degrees C. for 5.5 hrs., then the temperature was increased to 150 degrees C. and maintained at that temperature for 2.75 hrs., resulting in an % NCO value (ASTM D2572-87) of zero.

Infrared analysis confirmed the emergence of carbodiimide functionality (2125 cm$^{-1}$) and the disappearance of isocyanate functionality (2260 cm$^{-1}$) throughout the synthesis.

The non-volatile content was 76.2% measured at 110 degrees C./ 1 hr. and reduced to 51.7% with xylene. The carbodiimide equivalent weight (based on non-volatile) was 283 by procedure of Zarembo and Watts (*Microchem. J. Symp. Ser.*, 2,591 (1962), (293 theoretical equivalent weight). A weight average molecular weight of 2608 was determined by gel permeation chromatography relative to polystyrene standards.

EXAMPLE 3

A one liter, 3-neck flask, fitted with a condenser, an agitator, thermocouple and subsurface nitrogen inlet was charged with 117.3 gms. (0.48 moles) meta-tetramethylxylene diisocyanate, 82.7 gms. (0.32 moles) of methylene bis-(4-cyclohexyl isocyanate), 170.0 gms. of xylene, and 15.8 gms. (0.008 moles) of a 9.74 wt. % solution of 3-methyl-1-phenyl-2-phospholene-1-oxide in xylene. A nitrogen sparge was followed by a slow subsurface nitrogen stream that continued throughout the synthesis. Under agitation, the temperature was maintained at 145–150 degrees C. for 11 hrs. The temperature was reduced to 110 degrees C. and 23.7 gms. (0.32 moles) of n-butanol was charged to the mixture. The temperature was maintained at 110 degrees C. for 2.5 hrs., then the temperature was increased to 150 degrees C. and maintained at that temperature for 18 hrs. 15.8 gms. (0.008 moles) of a 9.74 wt. % solution of 3-methyl-1-phenyl-2-phospholene-1-oxide in xylene was then charged. The temperature was maintained at 145–150 degrees C. for 15.5 hrs., resulting in a % NCO value of 0.34% (ASTM D2572-87). The temperature was reduced to 110 degrees C. and 2.2 gms. (0.03 moles) of n-butanol was charged to consume the remainder of the unreacted isocyanate groups. The temperature was maintained at 110 degrees C. for 2 hours, resulting in a zero NCO value.

Infrared analysis confirmed the emergence of carbodiimide functionality (2125 cm$^{-1}$) and the disappearance of isocyanate functionality (2260 cm$^{-1}$) throughout the synthesis.

The non-volatile content was 54.2% measured at 110 degrees C./ 1 hr. The carbodiimide equivalent weight (based on non-volatile) was 297 by procedure of Zarembo and Watts (*Microchem, J. Symp. Ser.*, 2,591 (1962), (305 theoretical). A weight average molecular weight of 2662 was determined by gel permeation chromatography relative to polystyrene standards.

EXAMPLE 4

A one liter, 3-neck flask, fitted with a condenser, an agitator, thermocouple and subsurface nitrogen inlet was charged 161.2 gms. (0.66 moles) meta-tetramethylxylene diisocyanate, 97.8 gms. (0.44 moles) of isophorone diisocyanate, 230.0 gms. of xylene, and 21.1 gms. (0.011 moles) of a 9.74 wt. % solution of 3-methyl-1-phenyl-2-phospholene-1-oxide in xylene. A nitrogen sparge was followed by a slow subsurface nitrogen stream that continued throughout the synthesis. Under agitation, the temperature was maintained at 145-150 degrees C. for 5.75 hrs. The temperature was reduced to 110 degrees C. and 33.1 gms. (0.44 moles) of n-butanol was charged to the mixture. The temperature was maintained at 110 degrees C. for 2 hrs., then the temperature was increased to 150 degrees C. and maintained at that temperature for 15 hrs., resulting in an % NCO value (ASTM D2572-87) of 0.07%. The temperature was reduced to 110 degrees C. and 1.1 gms. (0.008 moles) of n-butanol was charged to consume the remainder of the residual isocyanate groups. The temperature was maintained at 110 degrees C. for 2 hrs., resulting in an NCO value of zero.

Infrared analysis confirmed the emergence of carbodiimide functionality (2125 cm$^{-1}$) and the disappearance of isocyanate functionality (2260 cm$^{-1}$) throughout the synthesis.

The non-volatile content was 52.0% measured at 110 degrees C./ 1 hr. The carbodiimide equivalent weight (based on non-volatile) was 297 by procedure of Zarembo and Watts (*Microchem. J. Symp. Ser.*, 2,591 (1962), (287 theoretical equivalent weight). A weight average molecular weight of 2662 was determined by gel permeation chromatography relative to polystyrene standards.

EXAMPLE 5

A one liter, 3-neck flask, fitted with a condenser, an agitator, thermocouple and subsurface nitrogen inlet was charged with 177.8 gms. (0.80 moles) of isophorone diisocyanate, 162.0 gms. of xylene, and 15.8 gms. (0.008 moles) of a 9.74 wt. % solution of 3-methyl-1-phenyl-2-phospholene-1-oxide in xylene. A nitrogen sparge was followed by a slow subsurface nitrogen stream that continued throughout the synthesis. Under agitation, the temperature was maintained at 145-150 degrees C. for 1.5 hrs. The temperature was reduced to 110 degrees C. and 23.7 gms. (0.32 moles) of n-butanol was charged to the mixture. The temperature was maintained at 110 degrees C. for 3.5 hrs., then the temperature was increased to 150 degrees C. and maintained at that temperature for 7.25 hrs., resulting in an % NCO value (ASTM D2572-87) of zero.

Infrared analysis confirmed the emergence of carbodiimide functionality (2125 cm$^{-1}$) and the disappearance of isocyanate functionality (2260 cm$^{-1}$) throughout the synthesis.

The non-volatile content was 53.8% measured at 110 degrees C./ 1 hr. The carbodiimide equivalent weight (based on non-volatile) was 276 by procedure of Zarembo and Watts (*Microchem. J. Symp. Ser.*, 2,591 (1962), (271 theoretical equivalent weight). A weight average molecular weight of 3174 was determined by gel permeation chromatography relative to polystyrene standards.

EXAMPLE 6

A one liter, 3-neck flask, fitted with a condenser, an agitator, thermocouple and subsurface nitrogen inlet was charged with 207.7 gms. (0.80 moles) of methylene bis-(4-cyclohexyl isocyanate), 172.0 gms. of xylene, and 15.8 gms. (0.008 moles) of a 9.74 wt. % solution of 3-methyl-1-phenyl-2-phospholene-1-oxide in xylene. A nitrogen sparge was followed by a slow subsurface nitrogen stream that continued throughout the synthesis. Under agitation, the temperature was maintained at 145-150 degrees C. for 4 hrs. Another 7.9 gms. (0.004 moles) of a 9.74 wt. % solution of 3-methyl-1-phenyl-2-phospholene-1-oxide in xylene was charged to the mixture and the temperature maintained at 145-150 degrees C. for 8 hrs. The temperature was reduced to 110 degrees C. and 23.7 gms. (0.32 moles) of n-butanol was charged to the mixture. The temperature was maintained at 110 degrees C. for 2 hrs., resulting in a % NCO value (ASTM D2572-87) of zero.

Infrared analysis confirmed the emergence of carbodiimide functionality (2125 cm$^{-1}$) and the disappearance of isocyanate functionality (2260 cm$^{-1}$) throughout the synthesis.

The non-volatile content was 53.1% measured at 110 degrees C./ 1 hr. The carbodiimide equivalent weight (based on non-volatile) was 311 by procedure of Zarembo and Watts (*Microchem. J. Symp. Ser.*, 2,591 (1962), (316 theoretical equivalent weight). A weight average molecular weight of 3665 was determined by gel permeation chromatography relative to polystyrene standards.

EXAMPLE 7

Example 7 was prepared according to example 6 of U.S. Pat. No. 4,977,219.

EXAMPLE 8

Example 8 was prepared according to example 2 of U.S. Pat. No. 5,008,363.

COATING COMPOSITIONS

Coating compositions were prepared using the Synthemul ® 40-425 (Reichhold Chemicals Inc.) acid functional resin as the cross-linkable component. The coating compositions were each reduced to 30% non-volatile and evaluated for gel times. The carbodiimide component was added last. The formulations and gel times are listed in the table below:

| EXAMPLE | GMS. 40425 | GMS. E-1 | GMS. E-2 | GMS. E-3 | GMS. E-4 | GMS. E-5 | GMS. E-6 | GMS. E-7 | GMS. E-8 | GMS. XYLENE | MINS. GEL |
|---|---|---|---|---|---|---|---|---|---|---|---|
| F-1 | 12.5 | 5.78 | | | | | | | | 18.75 | 540 |
| F-2 | 12.5 | | 5.37 | | | | | | | 18.00 | 13 |
| F-3 | 12.5 | | | 5.63 | | | | | | 19.14 | 10 |
| F-4 | 12.5 | | | | 5.53 | | | | | 18.64 | 7 |
| F-5 | 12.5 | | | | | 5.04 | | | | 18.59 | 1 |
| F-6 | 12.5 | | | | | | 5.96 | | | 19.14 | 1 |
| F-7 | 12.5 | | | | | | | 3.89 | | 16.55 | 1 |
| F-8 | 12.5 | | | | | | | | 6.30 | 18.33 | 2.5 |
| F-9 | 12.5 | 3.47 | | | | | 2.35 | | | 18.96 | 2 |
| F-10 | 12.5 | 4.62 | | | 1.01 | | | | | 18.72 | 8.5 |

We claim:

1. A carbodiimide compound having the formula:

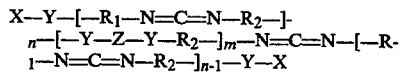

Wherein:

m is from 0 to 1 n is from 1 to 10

$R_1$ = A divalent hydrocarbon residue from a diisocyanate having a tertiary hydrocarbon selected from the group consisting of:

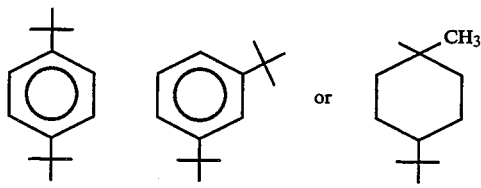

$R_2$ = A divalent hydrocarbon residue from a diisocyanate selected from:

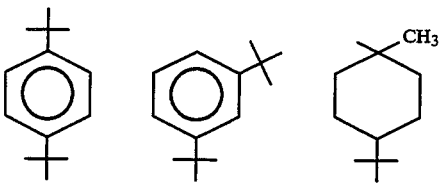

or residues from aliphatic, branched aliphatic or cycloaliphatic diisocyanates, biurets, allophonates, isocyanurates or uretdiones thereof.

X = Any radical with substituents that are unreactive towards a carbodiimide.

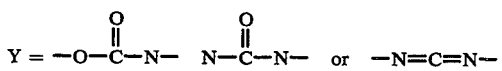

Z = A polyvalent radical with substituents that are unreactive towards a carbodiimide to function as an extending or branching site.

2. A compound according to claim 1 wherein n=2 to 5 and m=0.

3. A compound according to claim 1 wherein n=2 to 5 and m=1.

4. A compound according to claim 1 wherein X is a radical selected from the group consisting of aliphatic, branched aliphatic, cycloaliphatic, aromatic hydrocarbon, organosilane and salted sulfonic acid radicals.

5. A compound according to claim 1 wherein X is a polymeric radical selected from polyether and polyester.

6. A compound according to claim 1 wherein Z is a radical selected from the group consisting of aliphatic, branched aliphatic, cycloaliphatic, aromatic hydrocarbon, organosilane and salted sulfonic acid radicals.

7. A compound according to claim 1 wherein Z is a polymeric radical selected from polyether and polyester.

* * * * *